United States Patent [19]

Duffett

[11] Patent Number: Plant 5,619

[45] Date of Patent: Dec. 31, 1985

[54] CHRYSANTHEMUM PLANT NAMED TAN

[75] Inventor: William E. Duffett, Salinas, Calif.

[73] Assignee: Yoder Brothers, Inc., Barberton, Ohio

[21] Appl. No.: 574,721

[22] Filed: Jan. 27, 1984

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant known by the cultivar name Tan and particularly characterized as to uniqueness by the combined characteristics of flat capitulum form; daisy capitulum type; greyed orange ray floret color; diameter across face of capitulum ranging from 5 to 6.25 cm. at maturity; uniform eight week flowering response; medium plant height; semi-spreading branching pattern; and tolerance of both low winter 13° C. to 21° C. and high summer 18° C. to 32° C. temperatures for bud initiation and flower development.

3 Drawing Figures

The present invention comprises a new and distinct cultivar of *Chrysanthemum morifolium*, Ramat., named Tan.

Tan is a product of a planned breeding program which had the objective of creating new chrysanthemum cultivars for pinched spray pot mum programs having daisy capitulum type, orange floret color, eight week flowering response and the ability to produce commercially acceptable quality in year round programs. Such traits in combination were not present or required improvements in previously available commercial cultivars.

Tan was originated from a cross made in a controlled breeding program in Salinas, Calif. in 1979. The female parent was Sunny Mandalay, disclosed by U.S. Plant Pat. No. 3,231 and originated by the present inventor as a mutation from Yellow Mandalay. The male parent of Tan was an unnamed seedling identified as 79029004, originated from a cross between Mandarin, unpatented, commercially available and an unnamed seedling identified as 71078021.

Tan was discovered and selected as one flowering plant within the progeny of the stated cross by William E. Duffett in June 1980 in a controlled environment in Salinas, Calif.

The first act of asexual reproduction of Tan was accomplished when vegetative cuttings were taken from the initial selection in October 1980 in a controlled environment in Salinas, Calif. by a technician working under formulations established and supervised by William E. Duffett. Horticultural examination of selected units initiated October 1981 has demonstrated that the combination of characteristics as herein disclosed for Tan are firmly fixed and are retained through successive generations of asexual reproduction.

Tan has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Tan which in combination distinguish this chrysanthemum as a new and distinct cultivar:

(1) Flat capitulum form.

(2) Daisy capitulum type.

(3) Greyed orange ray floret color.

(4) Diameter across face of capitulum ranging from 5 to 6.25 cm. at maturity.

(5) Uniform eight week photoperiodic flowering response to short days.

(6) Medium plant height (requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6" pots).

(7) Semi-spreading branching pattern.

(8) Tolerance of low winter 13° C. to 21° C. temperatures.

(9) Tolerance of high summer 18° C. to 32° C. temperatures.

The accompanying photographic drawings depict typical leaf and inflorescence characteristics of Tan. Sheet 1 is a color photograph of a plant of Tan grown as a pinched spray pot mum, with colors being as accurate as possible with renditions of this type. Sheet 2 is a black and white photograph of three views of the inflorescence of Tan. Sheet 3 shows the leaves of Tan in three stages of growth (mature, intermediate, immature).

Of the many commercial cultivars known to the present inventor, the most similar in comparison to Tan is Cirbronze, disclosed in U.S. Plant Pat. No. 4,492. Reference is made to attached Chart A which compares certain characteristics of Tan to those same characteristics of Cirbronze.

Similar traits are the capitulum form, type and diameter, plant height and branching pattern. Tan has a faster response time, a lighter, greyed orange ray floret color, and its tolerance of lower temperatures results in more uniform flowering.

In the following description, color references are made to The Royal Horticultural Society Colour Chart. The color values were determined between 4:00 P.M. and 4:30 P.M. on Oct. 26, 1983 under 150 foot-candle light intensity at Salinas, Calif.

Classification:

*Botanical.*—*Chrysanthemum morifolium.* Ramat. cv Tan.

*Commercial.*—Daisy spray pot mum.

I. Inflorescence:

A. *Capitulum.*—Form: Flat. Type: Daisy. Diameter Across Face: 5 to 6.25 cm.

B. *Corolla of ray florets.*—Color (General tonality from a distance of three meters): Greyed Orange. Color (abaxial): 169 B-C oxidizing to between 22A and 23 A. Color (adaxial): 163 B-C suffused with 163A. Shape: Oblong, rounded tip.

C. *Corolla of disc florets.*—Color (mature): 1A. Color (immature): 154A.

D. *Reproductive organs.*—Androecium: Present disc florets only; moderate pollen. Gynoecium: Present both ray and disc florets.

II. Plant:

A. *General appearance.*—Height: Medium. Branching Pattern: Spreading.

B. *Foliage.*—Color (abaxial): 147A. Color (adaxial): 137C. Shape: Shallow lobed. Smooth with minimum serration.

CHART A

COMPARISON OF TAN AND CIRBRONZE

| CULTIVAR | RAY FLORET COLOR | CAPITULUM FORM AND TYPE |
|---|---|---|
| TAN | GREYED ORANGE | FLAT DAISY |
| CIRBRONZE | MEDIUM BRONZE | FLAT DAISY |

| | BRANCHING | DIAMETER ACROSS FACE OF |
|---|---|---|

CHART A-continued

COMPARISON OF TAN AND CIRBRONZE

| CULTIVAR | PATTERN | CAPITULUM |
|---|---|---|
| TAN | SEMI-SPREADING | 5 to 6.25 cm. |
| CIRBRONZE | SEMI-SPREADING | 5.5 to 7.5 cm. |

| CULTIVAR | PLANT HEIGHT | FLOWERING RESPONSE PERIOD | TEMPERATURE TOLERANCE |
|---|---|---|---|
| TAN | MEDIUM 25 to 35 cm. | 8 WEEK | 13° C. to 21° C. UNIFORM 18° C. to 32° C. UNIFORM |
| CIRBRONZE | MEDIUM 30 to 45 cm. | 9 WEEK | 13° C. to 21° C. UNEVEN 18° C. to 32° C. UNIFORM COLOR DULLS |

COMPARISONS MADE OF PLANTS GROWN AS PINCHED SPRAY POT MUMS IN SALINAS, CALIFORNIA AND LEAMINGTON, ONTARIO, CANADA

I claim:

1. A new and distinct cultivar of *Chrysanthemum morifolium,* Ramat., plant named Tan, as described and illustrated, and particularly characterized as to uniqueness by the combined characteristics of flat capitulum form; daisy capitulum type; greyed orange ray floret color; diameter across face of capitulum ranging from 5 to 6.25 cm. at maturity; uniform eight week flowering response; medium plant height; semi-spreading branching pattern; and tolerance of both low winter 13° C. to 21° C. and high summer 18° C. to 32° C. temperatures for bud initiation and flower development.

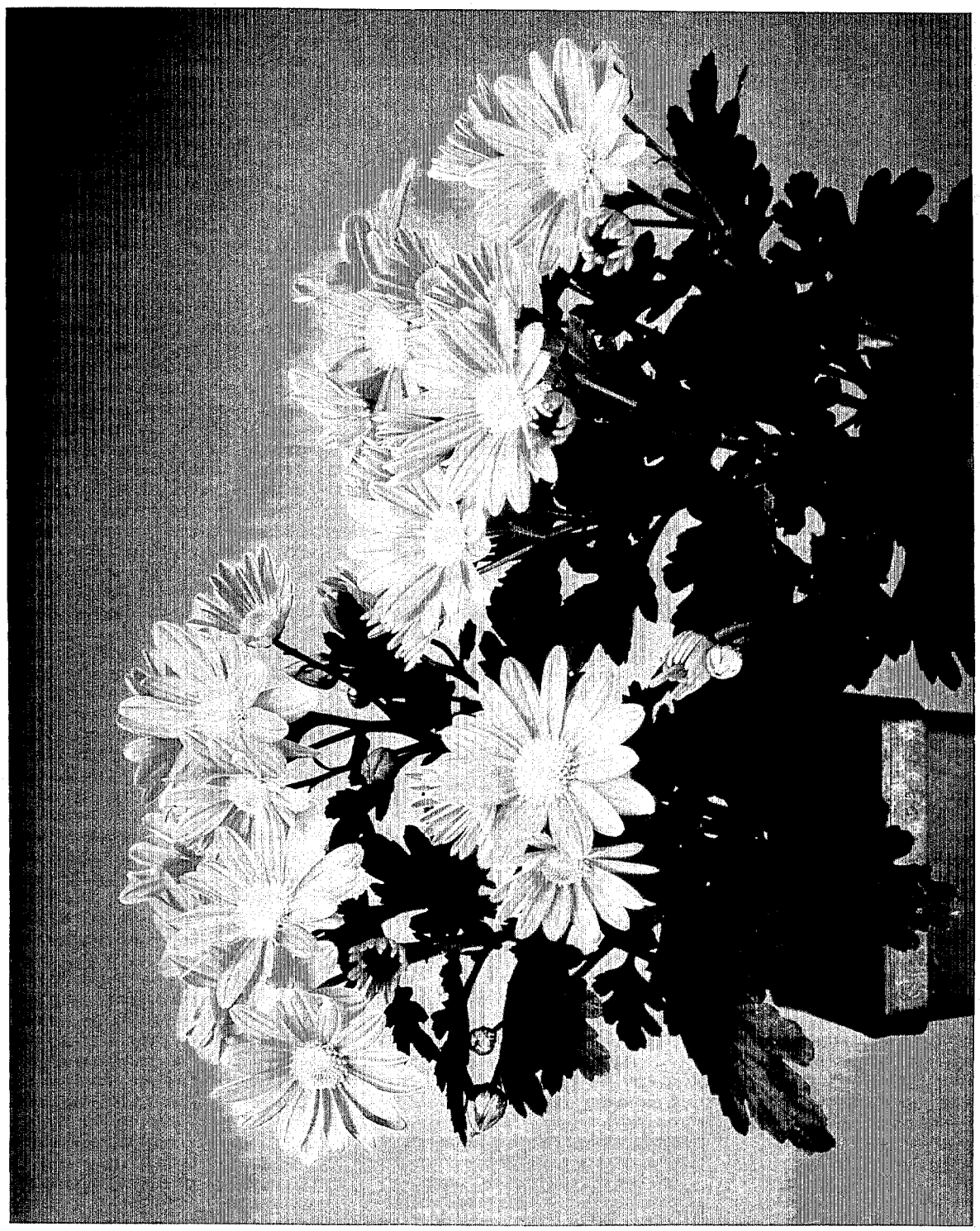

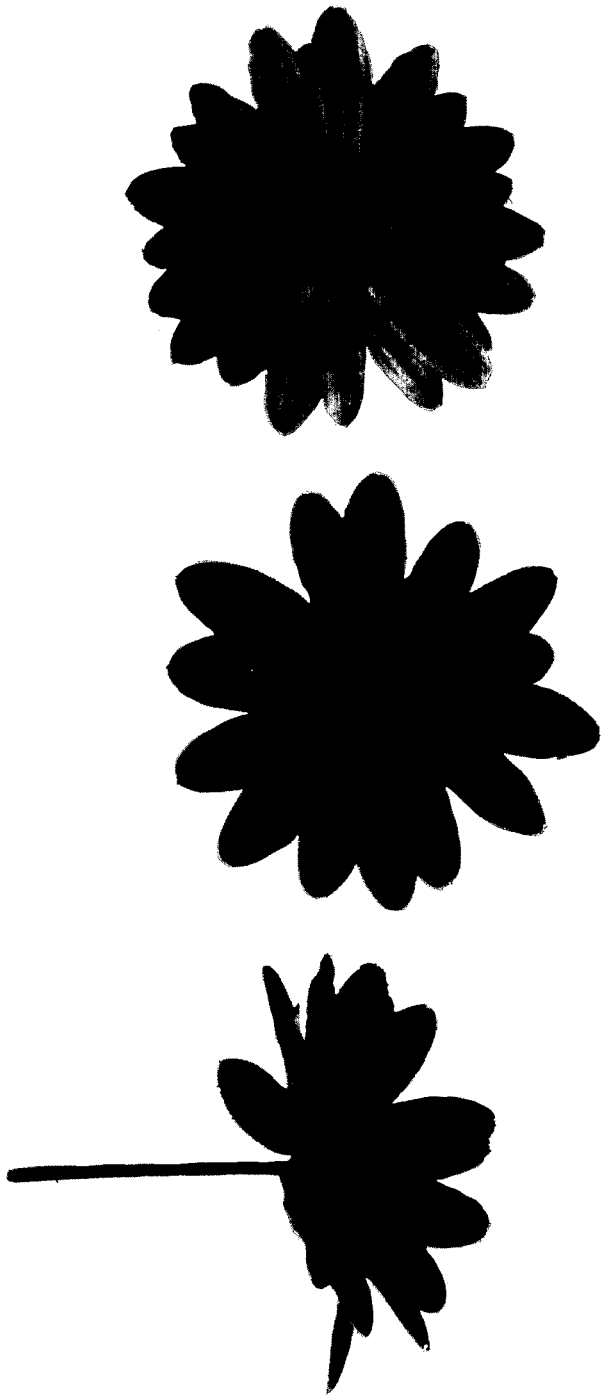

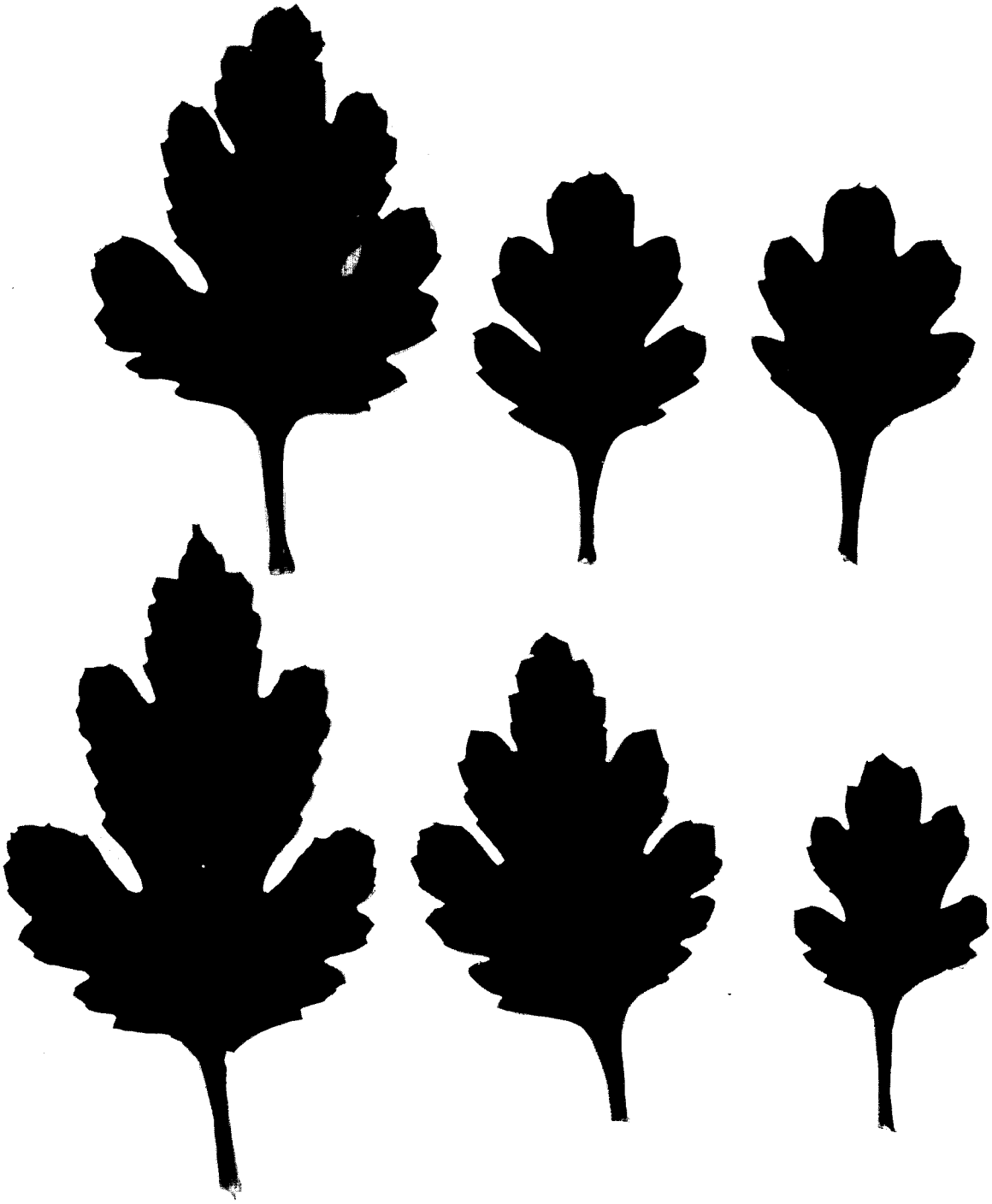

* * * * *